United States Patent
Curry

(10) Patent No.: US 6,673,366 B1
(45) Date of Patent: Jan. 6, 2004

(54) BREAST ENHANCEMENT SYSTEM

(76) Inventor: Susan C. Curry, 2670 Chandler Ave., Suite 5, Las Vegas, NV (US) 89120

( * ) Notice: Subject to any disclaimer, the term of this patent is extended or adjusted under 35 U.S.C. 154(b) by 0 days.

(21) Appl. No.: 10/458,993

(22) Filed: Jun. 10, 2003

(51) Int. Cl.$^7$ ............................. A61K 9/48; A61K 9/64; A61K 9/20; A61K 35/78

(52) U.S. Cl. ........................ 424/451; 424/456; 424/464; 424/725; 424/727; 424/757; 424/776; 424/777; 424/778

(58) Field of Search .................................. 424/451, 456, 424/464, 725, 727, 757, 776, 777, 778

(56) References Cited

U.S. PATENT DOCUMENTS

2003/0018009 A1 * 1/2003 Collins

OTHER PUBLICATIONS

Nature's Way 2 for 12, PMS Forumula, Jun. 03, 2003, Website printout 2 pages.

Dr. Christopher's Changease, Plant Hormones for Women, Jun. 03, 2003, Website printout 1 page.

Natrol, PMS Control for Women, Jun. 03, 2003, Website printout 3 pages.

* cited by examiner

*Primary Examiner*—Thurman K. Page
*Assistant Examiner*—Humera N. Sheikh

(57) ABSTRACT

A breast enhancement system for reducing the symptoms of PMS and/or non-invasive breast augmentation. The composition includes an amount of saw palmetto extract, an amount of soybean extract, an amount of pomegranate extract, an amount of wild yam extract, an amount of fennel seed, an amount of dong quai, an amount of blessed thistle, an amount of dandelion root and an amount of watercress. The composition is preferably distributed in an oral system, preferably in the form of a plurality of capsule, caplet, tablets, soft gelatin capsule or the like taken separately, orally administered on a daily basis.

5 Claims, No Drawings

BREAST ENHANCEMENT SYSTEM

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to natural breast enhancement aides and more specifically it relates to a breast enhancement system for reducing the symptoms of PMS and/or non-invasive breast augmentation.

2. Description of the Related Art

Breast enhancement systems have typically been comprised of surgical breast augmentation. Surgical breast augmentation is evasive, potentially dangerous, costly, leaves scars and difficult to reverse after implementation.

Hence, natural breast enhancement systems have been developed recently as an alternative to invasive surgical procedures. Examples of products on the market today are NATURE'S WAY PMS FORMULA, DR. CHRISTOPHER'S CHANGEASE, and NATROL PMS CONTROL FOR WOMEN.

Breast augmentation and/or maintenance in young and older females are major personal desires of, and social demand placed on millions of women throughout the world. Genetics and the natural hormones responsible for desirable bust lines are not the same in all females. Technology advances in the apparel, medical, and cosmetic industries have attempted to satisfy the demands of the general population, but more often leave much to be desired or too much to be handled. It is commonly known that breast enhancement occurs naturally in most women during the latter half of the normal menstrual cycle.

In these respects, the breast enhancement system according to the present invention substantially departs from the conventional methods of use and compositions of the prior art, and in so doing provides a composition and a method of using the composition primarily developed for the purpose of reducing the symptoms of PMS and/or non-invasive breast augmentation.

BRIEF SUMMARY OF THE INVENTION

In view of the foregoing disadvantages inherent in the known types of invasive breast augmentation systems now present in the prior art, the present invention provides a new breast enhancement system wherein the same can be utilized for reducing the symptoms of PMS and/or non-invasive breast augmentation.

The general purpose of the present invention, which will be described subsequently in greater detail, is to provide a new breast enhancement system that has many of the advantages of existing natural breast augmentation systems mentioned heretofore and many novel features and functions that result in a new breast enhancement system which is not anticipated, rendered obvious, suggested, or even implied by any of the prior art natural breast augmentation systems, either alone or in any combination thereof.

To attain this, the present invention generally comprises an amount of saw palmetto extract, an amount of soybean extract, an amount of pomegranate extract, an amount of wild yam extract, an amount of fennel seed, an amount of dong quai, an amount of blessed thistle, an amount of dandelion root and an amount of watercress. The composition is preferably distributed in an oral system, preferably in the form of a plurality of capsules, caplet, tablets, soft gelatin capsule or the like taken separately, orally administered on a daily basis.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in drawings. The invention is capable of other embodiments and of being practiced and carried out in various ways. Also, it is to be understood that the phraseology and terminology employed herein are for the purpose of the description and should not be regarded as limiting.

A primary object of the present invention is to provide a breast enhancement system that will overcome the shortcomings of the prior art.

Another object is to provide a breast enhancement system that reduces the symptoms of premenstrual syndrome (PMS) and/or non-invasive breast augmentation.

An additional object is to provide a breast enhancement system that is non-invasive.

A further object is to provide a breast enhancement system that does not leave scars.

Another object is to provide a breast enhancement system that enhances the breast size by mimicking natural hormones.

A further object is to provide a breast enhancement system that may be taken orally in the form of a capsule, caplet, tablet, soft gelatin capsule or the like.

Another object is to provide a breast enhancement system that improves an individual's quality of life and self-confidence.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific use illustrated and described within the scope of the appended claims.

DETAILED DESCRIPTION OF THE INVENTION

The composition an amount of saw palmetto extract, an amount of soybean extract, an amount of pomegranate extract, an amount of wild yam extract, an amount of fennel seed, an amount of dong quai, an amount of blessed thistle, an amount of dandelion root and an amount of watercress. The composition is preferably distributed in an oral system, preferably in the form of a plurality of capsules, caplet, tablet, soft gelatin capsule or the like taken separately, orally administered on a daily basis for a sufficient period of time.

The composition includes from about 2.0% to about 5.0% by weight of the ascorbic acid (vitamin C). The composition preferably includes about 3.0% by weight of the ascorbic acid.

The composition further includes from about 7.0% to about 14.0% by weight of the D-alpha tocopheryl acetate (vitamin E). The composition preferably includes about 8.0% by weight of the D-alpha tocopheryl acetate.

The composition includes from about 6.0% to about 10.0% by weight of soybean extract (*glycine max*). The composition preferably includes about 7.0% by weight of soybean extract. Soybean extract comes from the Fabaceae (Papilionaceae) or Leguminosae family. In addition to whole soybean, foods derived from soybeans are also available as a supplement, as soy protein or isoflavones. Soybeans are isolate/concentrated soy proteins and soy extracts which contain a high amount of compounds called isoflavones. The isoflavones have been associated with a wide variety of beneficial health effects, such as menopause, osteoporosis, hot flashes, PMS, reduction in serum cholesterol and may protect against the development of coronary heart disease.

The composition further includes from about 30.0% to about 60.0% by weight of saw palmetto extract (*serenoa repens*), with preferably about 40.0% by weight of saw palmetto extract. Saw palmetto extract comes from a dwarf palm tree. Saw Palmetto is used as a general tonic to nourish the body. Saw Palmetto is used for male disorders as well as for infertility, painful periods, and lactation in women. Saw Palmetto also has a phytosterol and fatty acid profile.

The composition also includes from about 3.0% to about 5.0% by weight of pomegranate extract (*punica granatum*), with preferably about 4.0% by weight of pomegranate extract. Pomegranate extract has demonstrated a variety of beneficial functions including antioxidant and anti-viral, mild astringent and an excellent free radical scavenger. Pomegranate extract is primarily composed of alkaloids and polyphenols. The active constituent that appears to be responsible for its multiple health benefits is Ellagic acid content. Ellagic acid is a polyphenol that has the ability to inhibit the growth of cancer cells. Polyphenols are substantially subdivided into 2 groups flavonoids and anthocyanins.

The composition includes from about 0.5% to about 2.0% by weight of wild yam extract (*dioscorea villosa*), with preferably about 2.0% by weight of wild yam extract. Wild yam has been helpful for women to relieve menopause and PMS symptoms. Wild yam is used as an antispasmodic, for cramps, an antioxidant, and an anti-inflammatory. One of wild yam's main active constituent is diosgenin, which is a sapogenin chemical of the saponin group. Saponin is a glycosidic surfactants produced by plant cells.

The composition also includes from about 8.0% to about 12.0% by weight of fennel seed (*foeniculum vulgare*), with preferably about 9.0% by weight of fennel seed. Fennel seed has been used to promote menstruation in women. Fennel seed may show to have a mild estrogenic effect (i.e. acts like the female hormone estrogen). This may be responsible for the use of fennel seed for milk production and for stimulating menstruation. Fennel seed may also be useful to relieve the pains of menopause in older women.

The composition includes from about 8.0% to about 12.0% by weight of dong quai (*angelica sinensis*), with preferably 9.0% by weight of dong quai. Dong Quai may show benefits for abnormal menstruation, suppressed menstrual flow, painful or difficult menstruation, and uterine bleeding. Dong quai was traditionally used for hot flashes. Dong quai has also been used as the female tonic for regulating female hormones.

The composition further includes from about 6.0% to about 10.0% by weight of blessed thistle (*cnicus benedictus*), with preferably about 7.0% by weight of blessed thistle. Blessed thistle has a long history for stimulating milk production in nursing mothers, relieving cramps, painful menstruation, treating headaches associated with female cycles, balances female hormones, promotes lactation, enriches breast milk, and strengthens the body during pregnancy.

The composition also includes from about 4.0% to about 6.0% by weight of dandelion root (*taraxacum officinale*), with preferably about 5.0% by weight of dandelion root. Dandelion may act as a mild diuretic, helping the body to rid itself of excess water. Dandelion's gentle stimulating action on the liver is especially useful for PMS sufferers, who frequently experience bloating in the week preceding a period.

The composition includes from about 4.0% to about 6.0% by weight of watercress (*nasturtium officinale*), with preferably about 5.0% by weight of watercress. As a member of the cabbage family, Watercress contains good amounts of antioxidants like Vitamin A and C. Studies have shown that consumption of vegetables can protect the body against cancers. Watercress is also used as a general tonic.

The composition is preferably combined into the form of a capsule, caplet, tablet, soft gelatin capsule or the like for oral consumption by a human being. Other ingredients may be included within the composition to make the product suitable for commercial sale and consumption such as silicon dioxide, magnesium stearate gelatin and water. The composition may be taken daily or at prescribed intervals to achieve the desired breast augmentation. It may take 5–8 weeks to experience results from this product and results may vary.

As to a further discussion of the manner of usage of the present invention, the same should be apparent from the above description. Accordingly, no further discussion relating to the manner of usage will be provided.

With respect to the above description then, it is to be realized that the optimum relationships for the components of the invention, to include variations in proportions and manner of use are deemed readily apparent and obvious to one skilled in the art.

Therefore, the foregoing is considered as illustrative only of the principles of the invention. Further, since numerous modifications and changes will readily occur to those skilled in the art, it is not desired to limit the invention to the exact composition and use shown and described, and accordingly, all suitable modifications and equivalents may be resorted to, falling within the scope of the invention.

I claim:

1. An orally administered composition for breast augmentation and/or reducing premenstrual syndrome symptoms in a human female, comprising:

from about 30.0% to about 60.0% by weight of saw palmetto extract;

from about 5.0% to about 15.0% by weight of soybean extract;

from about 3.0% to about 5.0% by weight of pomegranate extract;

from about 0.5% to about 2.0% by weight of wild yam extract;

from about 8.0% to about 12.0% by weight of fennel seed;

from about 8.0% to about 12.0% by weight of dong quai;

from about 6.0% to about 10.0% by weight of blessed thistle;

from about 4.0% to about 6.0% by weight of dandelion root; and from about 4.0% to about 6.0% by weight of watercress.

2. The composition of claim 1, wherein said composition comprises from about 7.0% to about 9.0% by weight of said soybean extract.

3. An orally administered composition for breast augmentation and/or reducing premenstrual syndrome symptoms in a human female, comprising:

from about 30.0% to about 60.0% by weight of saw palmetto extract;

from about 6.0% to about 10.0% by weight of soybean extract;

from about 3.0% to about 5.0% by weight of pomegranate extract;

from about 0.5% to about 2.0% by weight of wild yam extract;

from about 8.0% to about 12.0% by weight of fennel seed;

from about 8.0% to about 12.0% by weight of dong quai;

from about 6.0% to about 10.0% by weight of blessed thistle;

from about 4.0% to about 6.0% by weight of dandelion root; and from about 4.0% to about 6.0% by weight of watercress.

4. The composition of claim 3, wherein said composition comprises from about 7.0% to about 9.0% by weight of said soybean extract.

5. A method of treating a patient, consisting of orally taking a daily dosage of a composition comprising:

from about 30.0% to about 60.0% by weight of saw palmetto extract;

from about 6.0% to about 10.0% by weight of soybean extract;

from about 3.0% to about 5.0% by weight of pomegranate extract;

from about 0.5% to about 2.0% by weight of wild yam extract;

from about 8.0% to about 12.0% by weight of fennel seed;

from about 8.0% to about 12.0% by weight of dong quai;

from about 6.0% to about 10.0% by weight of blessed thistle;

from about 4.0% to about 6.0% by weight of dandelion root; and from about 4.0% to about 6.0% by weight of watercress.

* * * * *